United States Patent
Soula

(10) Patent No.: US 10,525,133 B2
(45) Date of Patent: Jan. 7, 2020

(54) AQUEOUS COMPOSITION COMPRISING AT LEAST ONE PROTEIN AND ONE SOLUBILIZING AGENT, PREPARATION THEREOF AND USES THEREOF

(71) Applicant: ADOCIA, Lyons (FR)

(72) Inventor: Rémi Soula, Lyons (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 15/694,534

(22) Filed: Sep. 1, 2017

(65) Prior Publication Data

US 2018/0214556 A1 Aug. 2, 2018

Related U.S. Application Data

(63) Continuation of application No. 14/712,328, filed on May 14, 2015, now abandoned.

(30) Foreign Application Priority Data

May 14, 2014 (FR) ...................... 14 54314

(51) Int. Cl.

| A61K 47/12 | (2006.01) |
|---|---|
| C07K 16/06 | (2006.01) |
| A61K 47/18 | (2017.01) |
| A61K 9/00 | (2006.01) |
| A61K 47/22 | (2006.01) |
| A61K 9/08 | (2006.01) |
| A61K 39/395 | (2006.01) |
| A61K 38/00 | (2006.01) |

(52) U.S. Cl.
CPC ............ *A61K 47/12* (2013.01); *A61K 9/0019* (2013.01); *A61K 9/08* (2013.01); *A61K 39/39516* (2013.01); *A61K 39/39591* (2013.01); *A61K 47/183* (2013.01); *A61K 47/22* (2013.01); *C07K 16/06* (2013.01); *A61K 38/00* (2013.01); *C07K 2317/21* (2013.01)

(58) Field of Classification Search
None
See application file for complete search history.

(56) References Cited

U.S. PATENT DOCUMENTS

| 2,387,201 A | 10/1945 | Weiner |
|---|---|---|
| 2,847,385 A | 8/1958 | Hiler |
| 4,006,059 A | 2/1977 | Butler |
| 4,011,137 A | 3/1977 | Thompson et al. |
| 4,126,628 A | 11/1978 | Paquet |
| 4,438,029 A | 3/1984 | Erickson et al. |
| 4,472,385 A | 9/1984 | Brange et al. |
| 4,826,818 A | 5/1989 | Mori et al. |
| 5,204,366 A | 4/1993 | Lavanish et al. |
| 5,310,937 A | 5/1994 | Lavanish et al. |
| 5,929,027 A | 7/1999 | Takama et al. |
| 6,991,798 B1 | 1/2006 | Gschneidner et al. |
| 8,241,620 B2 | 8/2012 | Dahri-Correia et al. |
| 9,089,476 B2 | 7/2015 | Soula et al. |
| 2004/0131583 A1 | 7/2004 | Barritault et al. |
| 2004/0234616 A1 | 11/2004 | Sabetsky |
| 2005/0175611 A1 | 8/2005 | Mahler et al. |
| 2007/0191757 A1 | 8/2007 | Steiner et al. |
| 2007/0235365 A1 | 10/2007 | Pohl et al. |
| 2008/0014250 A1 | 1/2008 | Soula et al. |
| 2008/0039365 A1 | 2/2008 | Steiner et al. |
| 2008/0039368 A1 | 2/2008 | Steiner et al. |
| 2008/0096800 A1 | 4/2008 | Pohl et al. |
| 2008/0234227 A1 | 9/2008 | Soula et al. |
| 2009/0048412 A1 | 2/2009 | Soula et al. |
| 2009/0221805 A1 | 9/2009 | Dahri-Correia et al. |

(Continued)

FOREIGN PATENT DOCUMENTS

| CN | 1613862 A | 5/2005 |
|---|---|---|
| CN | 101835493 A | 9/2010 |

(Continued)

OTHER PUBLICATIONS

"Chemical Book" (downloaded online on Jan. 17, 2017 from URL:< http://www.chemicalbook.com/ProductChemical PropertiesCB7932982_EN.htm>) (Year: 2017).*

ChEBI-70976 (downloaded online on Jan. 17, 2017 from URL:<http://www.ebi.ac.uk/chebi/searchId.do;jsessionid=0C30621862A25C54A3A6EFBB1CFB84D0?chebild=CHEBI:70976>) (Year: 2017).*

"Sigma-Aldrich L-tryptophan" (downloaded online on Jan. 18, 2017 from URL:< http://www.sigmaaldrich.com/catalog/substance/ltryptophan204237322311 ?lang=en&region=US#>) (Year: 2017).*

"Sigma-Aldrich L-tyrosine" (downloaded online on Jan. 18, 2017 from URL:< http://www.sigmaaldrich.com/catalog/substance/ltyrosine181196018411 ?lang=en&region=US>) (Year: 2017).*

(Continued)

*Primary Examiner* — Sergio Coffa
(74) *Attorney, Agent, or Firm* — Oliff PLC

(57) ABSTRACT

The present invention relates to a liquid composition which comprises, in an aqueous medium, one or more protein(s) and one or more solubilizing agent(s) chosen from the group consisting of anionic compounds of non-saccharide structure, said structure of which contains at least one aromatic nucleus comprising at least 6 ring members (6 atoms) and at least one carboxylic acid group in salified form, and which has, in its acid form, a molar mass of between 130 and 500 g/mol.

It also relates to the use of said solubilizing agent(s) for preparing compositions according to the invention.

It also relates to a process for solubilizing one or more protein(s), wherein at least one solubilizing agent chosen from the group consisting of anionic compounds of non-saccharide structure, said structure of which contains at least one aromatic nucleus comprising at least 6 ring members (6 atoms) and at least one carboxylic acid group in salified form, and which has, in its acid form, a molar mass of between 130 and 500 g/mol, is added to an aqueous protein preparation in order to solubilize the protein.

10 Claims, No Drawings

(56) References Cited

U.S. PATENT DOCUMENTS

| | | |
|---|---|---|
| 2009/0291114 A1 | 11/2009 | Soula et al. |
| 2010/0137456 A1 | 6/2010 | Soula et al. |
| 2010/0166867 A1 | 7/2010 | Soula et al. |
| 2010/0167991 A1 | 7/2010 | Soula et al. |
| 2010/0184965 A1 | 7/2010 | Soula et al. |
| 2010/0227795 A1 | 9/2010 | Steiner et al. |
| 2010/0249020 A1 | 9/2010 | Soula et al. |
| 2011/0014189 A1 | 1/2011 | Soula et al. |
| 2011/0159068 A1 | 6/2011 | Soula et al. |
| 2011/0172166 A1 | 7/2011 | Charvet et al. |
| 2011/0195025 A1 | 8/2011 | Kett et al. |
| 2011/0195913 A1 | 8/2011 | Charvet et al. |
| 2011/0212901 A1 | 9/2011 | Akiyoshi et al. |
| 2011/0244530 A1 | 10/2011 | Toda et al. |
| 2011/0250653 A1 | 10/2011 | Toda et al. |
| 2011/0318429 A1 | 12/2011 | Ko |
| 2012/0041079 A1 | 2/2012 | Soula et al. |
| 2012/0094902 A1 | 4/2012 | Soula et al. |
| 2012/0178675 A1 | 7/2012 | Pohl et al. |
| 2012/0295833 A1 | 11/2012 | Charvet et al. |
| 2012/0309680 A1 | 12/2012 | Charvet et al. |
| 2013/0231281 A1 | 9/2013 | Soula et al. |
| 2014/0142034 A1 | 5/2014 | Soula et al. |
| 2014/0378373 A2 | 12/2014 | Soula et al. |

FOREIGN PATENT DOCUMENTS

| | | |
|---|---|---|
| CN | 101920019 A | 12/2010 |
| CN | 102300586 A | 12/2011 |
| DE | 103 55 251 A1 * | 6/2005 |
| EP | 0 093 551 A2 | 11/1983 |
| EP | 0 125 023 A1 | 11/1984 |
| EP | 0173494 A2 | 3/1986 |
| EP | 0 190 041 A2 | 8/1986 |
| EP | 0 214 826 A2 | 3/1987 |
| EP | 0125023 B1 | 6/1991 |
| EP | 0 441 563 A2 | 8/1991 |
| EP | 0608445 A1 | 8/1994 |
| EP | 0 648 495 A2 | 4/1995 |
| EP | 0 681 833 A2 | 11/1995 |
| EP | 0 700 683 A1 | 3/1996 |
| EP | 0 787 497 A2 | 8/1997 |
| EP | 1 623 979 A1 | 2/2006 |
| EP | 2 319 500 A1 | 5/2011 |
| EP | 2711077 A1 | 3/2014 |
| FR | 2 224 164 A1 | 10/1974 |
| FR | 2 914 305 A1 | 10/2008 |
| FR | 2 936 800 A1 | 4/2010 |
| FR | 2 943 538 A1 | 10/2010 |
| FR | 2 980 796 A1 | 4/2013 |
| JP | S47-22571 B | 11/1972 |
| JP | S61-12899 B2 | 4/1986 |
| JP | H03-153653 A | 7/1991 |
| JP | H07-82225 A | 3/1995 |
| JP | 2007/177182 A | 7/2007 |
| JP | 2007/177185 A | 7/2007 |
| JP | 2015/010075 A | 1/2015 |
| PL | 149145 B1 | 1/1990 |
| PT | 103003 A | 2/2005 |
| RU | 94026279 A | 6/1996 |
| WO | 88/06599 A1 | 9/1988 |
| WO | 90/10645 A1 | 9/1990 |
| WO | 91/009617 A1 | 7/1991 |
| WO | 96/33699 A1 | 10/1996 |
| WO | 97/49386 A1 | 12/1997 |
| WO | 99/34821 A1 | 7/1999 |
| WO | 00/064845 A1 | 11/2000 |
| WO | 02/20466 A1 | 3/2002 |
| WO | 02/053190 A2 | 7/2002 |
| WO | 03/000202 A2 | 1/2003 |
| WO | 03/014371 A1 | 2/2003 |
| WO | 03/57650 A2 | 7/2003 |
| WO | 2004/050620 A2 | 6/2004 |
| WO | 2004/093833 A2 | 11/2004 |
| WO | 2005/072803 A1 | 8/2005 |
| WO | 2005/089722 A1 | 9/2005 |
| WO | 2007/038773 A1 | 4/2007 |
| WO | 2007/041481 A1 | 4/2007 |
| WO | 2007/074456 A2 | 7/2007 |
| WO | 2007/116143 A1 | 10/2007 |
| WO | 2007/121256 A2 | 10/2007 |
| WO | 2008/038111 A1 | 4/2008 |
| WO | 2008/062466 A2 | 5/2008 |
| WO | 2008/084237 A2 | 7/2008 |
| WO | 2008/124522 A2 | 10/2008 |
| WO | 2008/152106 A1 | 12/2008 |
| WO | 2009/048945 A1 | 4/2009 |
| WO | 2009/048959 A1 | 4/2009 |
| WO | 2009/106386 A1 | 9/2009 |
| WO | 2009/127940 A1 | 10/2009 |
| WO | 2009/136500 A1 | 11/2009 |
| WO | 2010/018324 A1 | 2/2010 |
| WO | 2010/028055 A1 | 3/2010 |
| WO | 2010/041119 A1 | 4/2010 |
| WO | 2010/041138 A2 | 4/2010 |
| WO | 2010/053140 A1 | 5/2010 |
| WO | 2010/058106 A1 | 5/2010 |
| WO | 2010/067613 A1 | 6/2010 |
| WO | 2010/102020 A1 | 9/2010 |
| WO | 2010/122385 A1 | 10/2010 |
| WO | 2010/149772 A1 | 12/2010 |
| WO | 2011/077405 A1 | 6/2011 |
| WO | 2011/098962 A2 | 8/2011 |
| WO | 2012/002450 A1 | 1/2012 |
| WO | 2012/078760 A1 | 6/2012 |
| WO | 2012/124513 A1 | 9/2012 |
| WO | 2012/153070 A1 | 11/2012 |
| WO | 2012/153071 A2 | 11/2012 |
| WO | 2012/157656 A1 | 11/2012 |
| WO | 2013/021143 A1 | 2/2013 |
| WO | 2013/064787 A1 | 5/2013 |
| WO | 2014/076423 A1 | 5/2014 |
| WO | 2015/173377 A1 | 11/2015 |

OTHER PUBLICATIONS

Adediran, S.A. et al., "Deacylation Transition States of a Bacterial DD-Peptidase" Biochemistry, 45, 13074-13082 (2006).

Nov. 15, 2016 International Preliminary Report on Patentability issued in PCT Patent Application No. PCT/EP2015/060732.

Baudys, Miroslav et al., "Extending Insulin Action in Vivo by Conjugation to Carboxymethyl Dextran," Bioconjugate Chem. 1998, vol. 9, pp. 176-183.

Brange, Jens et al., "Insulin analogs with improved pharmacokinetic profiles," Advanced Drug Delivery Reviews, 1999, vol. 35, pp. 307-335.

Giger, Katie et al., "Suppression of Insulin Aggregation by Heparin," Biomacromolecules, 2008, vol. 9, pp. 2338-2344.

Lou, Xianwen et al., "Simulation of size exclusion chromatography for characterization of supramolecular complex: a theoretical study," Journal of Chromatography A, 2004, vol. 1029, pp. 67-75.

Tschantz, William R. et al., "Substrate Binding Is Required for Release of Product from Mammalian Protein Farnesyltransferase," The Journal of Biological Chemistry, 1997, vol. 272, No. 15, pp. 9989-9993.

Oct. 14, 2009 Search Report issued in French Patent Application No. 723351.

Jul. 12, 2010 Written Opinion issued in International Patent Application No. PCT/IB2010/000711.

Jul. 12, 2010 Search Report issued in International Patent Application No. PCT/IB2010/000711.

Sep. 19, 2012 Office Action issued in U.S. Appl. No. 12/662,036.

Arranz et al., "Water-insoluble dextrans by grafting, 3a) Reaction of dextran with butyl isocyanate. Chemical hydrolysis," Makromol. Chem., vol. 188, pp. 2831-2838, 1987.

Carpino et al., "Efficiency in Peptide Coupling: 1-Hydroxy-7-azabenzotriazole vs 3,4-Dihydro-3-hydroxy-4-oxo-1,2,3-benzotriazine," Journal of Organic Chemistry, vol. 60, pp. 3561-3564, 1995.

(56) References Cited

OTHER PUBLICATIONS

Caulfield et al., "The Permeability of Glomerular Capillaries to Graded Dextrans," The Journal of Cell Biology, vol. 63, pp. 883-903, 1974.
Chang et al., "Permselectivity of the glomerular capillary wall: III. Restricted transport of polyanions," Kidney International, vol. 8, pp. 212-218, 1975.
Demitras et al, Inorganic Chemistry, Prentice-Hall International Inc., 1972, enclosed pp. 1-5.
Engelmann et al., "Preparation of Starch Carbamates in Homogeneous Phase using Different Mixing Conditions," Starch/Stärke, 2001, pp. 560-569, vol. 53, Wiley-VCH Verlag GmbH.
Larsen, "Dextran prodrugs—structure and stability in relation to therapeutic activity," Advanced Drug Delivery Reviews, 1989, pp. 103-154, vol. 3, Elsevier.
Ouari et al., "Synthesis of a Glycolipidic Amphiphilic Nitrone as a New Spin Trap," J. Org. Chem., 1999, pp. 3554-3556, vol. 64, American Chemical Society (with 10 pages of supporting information).
Shen et al., "Synthesis and Characterization of Cellulose Carbamates Having alpha-Amino Acid Moieties," Polymer Bulletin, 2005, pp. 317-322, vol. 55.
Tsai et al., "Synthesis of Amino Acid Ester Isocyanates: Methyl (S)-2-Isocyanato-3-Phenylpropanoate [Benzenepropanoic acid, ?-isocyanato-, methyl ester, (S)]," Organic Syntheses Coll., vol. 10, p. 544, 2004; vol. 78, p. 220, 2002.
Won, "Synthesis of heterobifunctional poly(ethylene glycol) containing an acryloyl group at one end and an isocyanate group at the other end," Polymer Bulletin, 2004, pp. 109-115, vol. 52.
Definition of Phenylalanine, from Croatian English Chemistry Dictionary & Glossary (http://glossary.periodni.com/glossary.php?en=phenylalanine, enclosed, pp. 1-2, Accessed Jan. 17, 2013.
May 3, 2012 French Search Report issued in French Patent Application No. 1158885.
Feb. 22, 2013 Office Action issued in U.S. Appl. No. 12/662,036.
Feb. 28, 2013 Office Action issued in U.S. Appl. No. 13/468,799.
U.S. Appl. No. 12/662,036 to Soula et al., filed Mar. 29, 2010.
U.S. Appl. No. 13/287,793 to Soula et al., filed Nov. 2, 2011.
U.S. Appl. No. 13/468,799 to Charvet et al., filed May 10, 2012.
U.S. Appl. No. 13/468,849 to Charvet et al., filed Jul. 11, 2012.
Heinze et al.; "Functional Polymers Based on Dextran;" Adv. Polym. Sci.; 2006; pp. 199-291; vol. 205; Springer-Verlag Berlin Heidelberg.
May 28, 2014 Office Action issued in U.S. Appl. No. 13/468,849.
Jul. 24, 2013 Office Action issued in U.S. Appl. No. 12/662,036.
R. Janowski, et al., "Two Polymorphs of a Covalent Complex Between Papain and a Diazomethylketone Inhibitor," J. Peptide Res. 64, 2004, pp. 141-150.
Apr. 2, 2013 International Search Report issued in PCT/FR2012/052543.
Jun. 25, 2014 Office Action issued in U.S. Appl. No. 13/668,000.
Definition of derivative and analog, from http://cancerweb.ncl.ac.uk/omd/about.html, pp. 1-5, accessed Jul. 7, 2005.
Polymer Molecular Weight Distribution and Definitions of MW Averages, from www.agilent.com/chem, pp. 1-4, Jun. 10, 2011.
Dec. 12, 2011 French Search Report issued in French Patent Application No. 1154039.
Rudd, Pauline M. et al., "Glycoforms modify the dynamic stability and functional activity of an enzyme." Biochemistry (1994) 33 p. 17-22.
Memo, Myriad-Mayo guidance, Mar. 2014.
Bovine ribonuclease b sequence (protein data bank, accession No. 1RBJ_, upload Oct. 10, 2012).
Solomons, T.W. Graham; Organic Chemistry, 4th editon, (1988) ISBN 0-471-83659-1, p. 751.
Roussel et al., "Monolayer lipid membrane-forming dissymmetrical bolaamphiphiles derived from alginate oligosaccharides;" Chem. Communication; 2006; pp. 3622-3624.

Watanabe et al., "Synthesis of lipid A type carboxymethyl derivatives with ether chains instead of ester chains and their LPS-antagonistic "activities;" Carbohydrate" Research; 2003; pp. 47-54; vol. 338.
Song et al., 6-o-Amino-2-o-carboxymethyl Glucopyranoside as Novel Glycoaminoxy Acid Building Block for the Construction of Oligosaccharide Mimetics; Synthesis; 2011; pp. 2761-2766; No. 17.
Tareq et al., "Ieodoglucomides A and B from a Marine-Derived Bacterium Bacillus lichentiformis;" Organic Letters; 2012; pp. 1464-1467; vol. 14, No. 6.
Smoot et al., "Oligosaccharide Synthesis From Conventional Methods to Modern Expeditious Strategies;" Advances in Carbohydrate Chemistry and Biochemistry; 2009; pp. 161-251: vol. 62.
Pal et al., "Molecular mechanism of physical gelation of hydrocarbons by fatty acid amides of natural amino acids," Tetrahedron; 2007; pp. 7334-7348; vol. 63.
Bhaskar et al., "The Selective Silylation of d-Mannitol Assisted by Phenylboronic Acid and the Solid State and Solution Structures of the Intermediate 1,6-bis(silyl) bis(phenylboronates);"Journal of Carbohydrate Chemistry; 2003; pp. 867-879; vol. 22, 9.
Edwards et al., "Dispiroketals in Synthesis (Part 18): Regioselective and Enantioselective Protection of Symmetric Polyol Substrates Using an Enantiopure (2S,2S)-Dimethyl-bis-dihydropyran; Synlett"; 1995; pp. 898-900; vol. 9.
Ruiz-Pena et al., "Physico-chemical studies of molecular interactions between non-ionic surfactants and bovine serum albumin; Colloids" and Surfaces B: Biointerfaces: 2010: pp. 282-289; vol. 75.
Sawardeker, Jawahar S. et al., "Quantitative determination of monosaccharides as their alditol acetates by gas liquid chromatography." Anal. Chem. (1965) 37 (12) p. 1602-1604.
Class notes for physical chemistry form the Univesity of Washington http://www.ocean.washington.edu/courses/oc400/Lecture_Notes/CHPT6.pdf, Oct. 2004.
Granger, Elisabeth et al., "Simplified syntheses of complex multifunctional nanomaterials." Chem. Communication (2008) 4792-4794.
Oct. 15, 2014 Office Action issued in U.S. Appl. No. 14/079,437.
May 21, 2015 Office Action issued in U.S. Appl. No. 14/079,437.
U.S. Appl. No. 14/079,437, filed Nov. 13, 2013 in the name of Soula et al.
U.S. Appl. No. 14/581,239, filed Dec. 23, 2014 in the name of Soula et al.
U.S. Appl. No. 14/079,516, filed Nov. 13, 2013 in the name of Soula et al.
Dec. 18, 2015 Office Action issued in U.S. Appl. No. 14/079,437.
Wagner, Herman L., "The Mark-Houwink-Sakurada equation for the viscosity of linear polyethylene." J. Phys. Chem. Ref. Data (1985) 14(2) p. 611-617.
Wayne, Richard P., Principles and applications of photochemistry (1988) ISBN 0-19-855234-3.
Shimadzu scientific publication SC-AP-GC-0138, downloaded Dec. 1, 2015.
Dec. 21, 2015 Office Action issued in U.S. Appl. No. 14/079,516.
Jan. 22, 2016 Office Action issued in U.S. Appl. No. 14/581,239.
Jun. 10, 2016 Office Action Issued in U.S. Appl. No. 14/079,516.
Huus, Kasper et al., "Thermal Dissociation and Unfolding of Insulin", Biochemistry, 2005, vol. 44, pp. 11171-11177.
Uversky, Vladimir N. et al., "Prediction of the Association State of Insulin Using Spectral Parameters", Journal of Pharmaceutical Sciences, Apr. 2003, vol. 92, No. 4, pp. 847-858.
Lindhorst, Thisbe K., "O-Glycoside synthesis", Essentials of Carbohydrate Chemistry and Biochemistry, 2007, pp. 157-208.
Yalpani, Manssur et al., "Selective Chemical Modifications of Dextran", Journal of Polymer Science, 1985, vol. 23, pp. 1395-1405.
Cho, Byung Tae et al., "Direct and indirect reductive amination of aldehydes and ketones with solid acid-activated sodium borohydride under solvent-free conditions", Tetrahedron, 2005, vol. 61, pp. 5725-5734.
Zhang, Tianhong et al., "Novel Polysaccharide Surfactants: Synthesis of Model Compounds and Dextran-Based Surfactants", Macromolecules, 1994, vol. 27, pp. 7302-7308.

(56) References Cited

OTHER PUBLICATIONS

Takeoka, Shinji et al., "Physical properties and packing states of molecular assemblies of synthetic glycolipids in aqueous dispersions", Journal of the Chemical Society, Faraday Transactions, 1998, vol. 94, No. 15, pp. 2151-2158.
Sisu, Ioana et al., "Synthesis and structural characterization of amino-functionalized polysaccharides", Central European Journal of Chemistry, 2009, vol. 7, No. 1, pp. 66-73.
Kalra, Sanjay et al., "Ultra-fast acting insulin analogies", Recent Patents on Endocrine, Metabolic & Immune Drug Discovery, 2014, vol. 8-2, pp. 117-123.
May 17, 2016 Office Action Issued in U.S. Appl. No. 14/711,378.
Nov. 15, 2016 International Preliminary Report on Patentability issued in International Application No. PCT/EP2015/060716.
Kartvelishvili et al, Amino acid based bioanalogous polymers. Synthesis of novel poly(urethane amide)s based on N, N'-(trimethylenedioxy-dicarbonyl)bis(phenylalanine), Macromolecular Chemistry and Physics, 1996, 197, 249-257.
Coker et al, "Pathways for the Decay of Organic Dichloramines and Liberation of Antimicrobial Chloramine Gases", Chemical Research in Toxicology, 2008, 21(12), 2334-2343.
Schuster et al, "Chymotryspin-catalyzed peptide synthesis in ice: use of unprotected amino acids as acyl acceptors", Tetrahedron Letters, 1993, 34(36), 5701-5702.
Votano et al, "Inhibition of deoxyhemoglobin S polymerization by biaromatic peptides found to associate with the hemoglobin molecule at a preferred site", Biochemistry, 1985, 24, 1966-1970.
Gorecki et al, "Peptide inhibitors of sickle hemoglobin aggregation: effect of hydrophobicity", Biochemistry, 1980, 19(8), 1564-1568.
Behe et al, "Quantitative assessment of the noncovalent inhibition of sickle hemoglobin gelation by phenyl derivatives and other known agents", Biochemistry, 1979, 18(19), 4196-4201.
Khosla et al, "Synthesis of mixed Na, N?-peptides of lysine through direct N?-peptidation", Journal of Scientific and Industrial Research, Section B: Physical Sciences, 1962, 21B, 318-321.
Liwschitz et al, The reaction of N-maleoylamino acids with benzylamine, Journal of the Chemical Society, 1962, 3726-3729.
Huffman et al, "Substrate specificity of isopenicillin N synthase", Journal of Medicinal Chemistry, 1992, 35, 1897-1914.
Swamy et al, "Synthesis of iron (III), cobalt (II), nickel (II), copper (II) and zinc (II) complexes with new quadridentate N, O-donor ligands", Oriental Journal of Chemistry, 2008, 24(3), 1103-1106.
Bergeron; "An investigation of the Impact of Molecular Geometry upon Microcapsule Self-Assembly", Journal of American Chemical Society, 1995, 117(25), 6658-65.
Coker et al, Supporting information for "Antimicrobial activity of chlorinated amino acids and peptides." Chemical Research in Toxicology, 2008, 21(12), 1-11.
Tse et al, "Translation of a DNA into a Library of 13000 Synthetic Small-Molecule Macrocycles Suitable for in Vitro Selection", Journal of the American Chemical Society, 2008, 130(46), 15611-15626.
Liu et al, "Ring opening polymerization of aliphatic cyclic carbonates in the presence of natural amino acids", Journal of Applied Polymer Science, 2008, 107(5), 3275-3279.
Gartner et al, "Multistep small-molecule synthesis programmed by DNA templates", Journal of the American Chemical Society, 2002, 124(35), 10304-10306.
Siddique & Duhamel, "Effect of Polypeptide Sequence on Polypeptide Self-Assembly", Langmuir, 2011, 27(11), 6639-6650.
Sun et al, "Homo-cysteinyl peptide inhibitors of the L1 metallo-β-lactamase, and SAR as determined by combinatorial library synthesis", Bioorganic Medicinal Chemistry Letters, 2006, 16(19), 5169-5175.
Hong et al, "Determination of inhibitory constants for CPA by competitive spectrophotometry", Peptides: Biology and Chemistry, Proceedings of the Chinese Peptide Symposium, 5th, Lanzhou, China, Jul. 14-17, 1998 (2000).
Humme, "Amino acid derivatives hydrolyzable by an enzyme of rennet. III. Peptides", Nederlands Melk—en Zuiveltijdschrift, 1971, 25(1), 3-14.

Fruchart et al, "A new linker fot the synthesis of C-terminal peptide -oxo-aldehydes," Tetrahedron Letters, 1999, 40, 6225-6228.
U.S. Statutory Invention Registration No. H645, published Jun. 6, 1989.
Lodi et al, "Chiral aminoaci containing acyclic ligands. I. Syntheses and conformations", Tetrahedron, 1982, vol. 38, N° 14, pp. 2055-2060.
Feb. 6, 2015 Search Report issued in French Application No. 1454314.
Marchelli et al, "Chiral aminoaci containing acyclic ligands. II. Compexation of alkaline earth cations", Tetrahedron, 1982, vol. 38, N° 14, pp. 2061-2067.
Menzenski et al, "Self-assembly of supramolecular nanostructures from phenylalanine derived bolaamphiphiles", New Journal of Chemistry, 2007, vol. 31, pp. 1674-1680.
Jul. 22, 2016 Office Action Issued in U.S Appl. No. 14/712,696.
Nov. 15, 2016 International Preliminary Report on Patentability issued in PCT Patent Application No. PCT/EP2015/060820.
Wu et al.; Reactive Impurities in Excipients: Profiling, Identification and Mitigation of Drug-Excipient Incompatibility; AAPS PharmSciTech; Dec. 2011; pp. 1249-1263; vol. 12, No. 4.
Gildersleeve et al.; Improved Procedure for Direct Coupling of Carbohydrates to Proteins via Reductive Amination; Bioconjug Chem.; Jul. 2008; pp. 1485-1490; vol. 19, No. 7.
U.S Appl. No. 15/410,524, filed Jan. 19, 2017 in the name of Soula et al.
U.S Appl. No. 14/711,378, filed May 13, 2015 in the name of Soula et al.
U.S Appl. No. 14/712,696, filed May 14, 2015 in the name of Soula et al.
U.S Appl. No. 14/712,328, filed May 14, 2015 in the name of Soula.
U.S Appl. No. 15/353,522, filed Nov. 16, 2016 in the name of Soula et al.
Siddique & Duhamel, Supporting Information for "Effect of Polypeptide Sequence on Polypeptide Self-Assembly", Langmuir, 2011, 27(11), 6639-6650.
Apr. 27, 2016 Office Action issued in Chinese Application No. 201380059092.4.
"Chemical Book" (downloaded online on Jan. 17, 2017 from URL: <http://www.chemicalbook.com/ProductChemicalPropertiesCB7932982_EN.htm>).
ChEBI-70976 (downloaded online on Jan. 17, 2017 from URL: <http://www.ebi.ac.uk/chebi/searchId.do; sessionid=0C30621862A25C54A3A6EFBB1CFB84D0?chebiId=CHEBI:70976>).
"Sigma-Aldrich L-tryptophan" (downloaded online on Jan. 18, 2017 from URL: <http://www.sigmaaldrich.com/catalog/substance/ltrytophan204237322311&lang=en&region=US#>).
"Sigma-Aldrich L-tyrosine" (downloaded online on Jan. 18, 2017 from URL: <http://www.sigmaaldrich.com/catalog/substance/ltyrosine181196018411&lang=en&region=US>).
Mar. 7, 2017 Office Action issued in U.S Appl. No. 14/711,378.
Mar. 1, 2017 Office Action issued in U.S Appl. No. 14/712,328.
Feb. 8, 2017 Office Action issued in Chinese Application No. 201380059092.4.
Tse et al, "Translation of DNA into a Library of 13 000 Synthetic Small-Molecule Macrocycles Suitable for in Vitro Selection", Journal of the American Chemical Society, 2008, 130(46), with Supporting Information pp. 1-9.
Mar. 16, 2017 European Office Action issued in European Patent Application No. 13 801 655.5.
Apr. 21, 2017 Office Action issued in Chinese Patent Application No. 201380059136.3.
Apr. 26, 2017 Office Action issued in Japanese Patent Application No. 2015-542338.
Apr. 27, 2017 Office Action issued in Eurasian Patent Application No. 201590937/28.
Nov. 15, 2016 Search Report and Written Opinion issued in PCT Patent Application No. PCT/EP2015/060732.
Nov. 15, 2016 Search Report and Written Opinion issued in PCT Patent Application No. PCT/EP2015/060820.
Oct. 14, 2009 Search Report issued in French Application No. 09 01478.

(56) References Cited

OTHER PUBLICATIONS

Kabat et al., Sequences of proteins of immunological interest, 5th ed., U.S. Department of Health and Human Services, NIH, 1991m and later editions.
Morrison et al., Proc. Natl. Acad. Sci, U.S.A., 81, pp. 6851-6855 (1984).
Neuberger, M.S. et al., Nature 312 (5995): 604-8 (1985).
D. Saerens and S. Muyldermans, Single Domain Antibodies: Methods and Protocols, Methods in Molecular Biology, vol. 911; and Med Microbiol Immunol (2009).
Hollinger et al., Proc. Natl. Acad. Sci. USA 90: 6444-6448 (1993).
Pratt R. F. et al. Biochemistry, 2006, 45, 13074-13082.

* cited by examiner

AQUEOUS COMPOSITION COMPRISING AT LEAST ONE PROTEIN AND ONE SOLUBILIZING AGENT, PREPARATION THEREOF AND USES THEREOF

This is a Continuation of application Ser. No. 14/712,328 filed May 14, 2015, the entire disclosures of the prior application is hereby incorporated by reference herein their entirety.

The present invention relates to an aqueous composition comprising one or more protein(s) and at least one particular solubilizing agent. The invention also relates to the preparation of such a composition, and to the uses thereof in particular in the pharmaceutical and veterinary fields.

Finally, the invention relates to the use of particular compounds, in order to improve the solubilization of protein(s) within an aqueous composition.

The use of proteins of natural or synthetic origin in the form of solutions in a liquid medium is common, in particular in the pharmaceutical and veterinary fields, where it is necessary to be able to have liquid compositions containing protein active ingredients, intended to be administered to humans or to animals for therapeutic and/or prophylactic purposes. These liquid compositions must, as far as possible, be able to be formulated using water as solvent.

However, proteins can have a low solubility in an aqueous, or biological, medium and can give rise to unsatisfactory solubility, and in particular to unwanted precipitation phenomena.

The solubility of a protein in water depends to a large extent, on the one hand, on its structure and, on the other hand, on the pH. Indeed, depending on the pH, the protein may be in a more or less ionized form, which is capable of varying its solubility in water. The point where the solubility of a protein in water is the lowest is the isoelectric point (pI) of this protein, i.e. the pH at which the overall charge of the protein is zero.

Thus, when compositions comprising at least one protein are brought into contact with an aqueous medium, in particular when the pH of this medium corresponds to the isoelectric point of the protein, there is a need to improve the solubility of said protein, in particular in order to limit or avoid the precipitation thereof. This is particularly useful in the case of injection of the composition, in particular subcutaneous injection.

Quite particularly, there is a need to improve the solubility of proteins which have an isoelectric point around physiological pH (approximately 7.4) and which have problems of solubility in biological fluids, such as serum, blood, the subcutaneous space, etc.

Moreover, there is also a need to be able to formulate stable aqueous compositions containing proteins, which do not give rise to precipitation phenomena, whatever the pH of the composition, including at the isoelectric point of the proteins under consideration. For this, it has been proposed in the prior art to solubilize the proteins in water by means of water-soluble polymers such as, in particular, polysaccharides, which have the effect of interacting with the protein and promoting the solubilization thereof in water.

Thus, patent applications WO 2008/038111 and WO 2010/041119, filed in the name of Adocia, describe polysaccharides and/or oligosaccharides which have the property of creating interactions with active ingredients, in particular protein active ingredients.

These polymers consist of chains of which the lengths are statistically variable, and which are highly rich in possible sites of interaction with protein active ingredients. This multiple interaction potential could, however, create a lack of specificity in terms of interaction, whereas a smaller and better defined molecule could make it possible to be more specific in this respect.

Moreover, a polymer chain can interact with various sites present on a protein ingredient, but can also, owing to the length of the chain, interact with several protein ingredients, thereby leading to a bridging phenomenon. This bridging phenomenon may, for example, result in unwanted protein aggregation.

Furthermore, the use of polymeric compounds as solubilizing agents is not always desirable, in particular in the pharmaceutical field, since the elimination of such compounds by the organism can sometimes prove to be lengthy, or difficult. In addition, the use of such polymeric compounds often has the effect of increasing, sometimes considerably, the viscosity of the aqueous composition, which can be particularly problematic, in particular in the case of solutions intended to be administered by injection, in particular by subcutaneous injection.

In addition, polymers have the drawback of not being easily traceable (by mass spectrometry, for example) in biological media during pharmacokinetics or ADME (administration, distribution, metabolism, excretion) experiments, and generally give a diffuse signal with a high background noise in mass spectrometry.

Moreover, some solubilizing agents can be expensive and/or can require numerous synthesis, and optionally purification, steps.

Continuing its research in the field of the formulation of aqueous compositions containing proteins, and more particularly for the administration of protein active ingredients, the applicant has now demonstrated that, surprisingly, the use of certain non-polymeric compounds of particular structure makes it possible to significantly improve the solubility of proteins in an aqueous medium, while at the same time remedying all or some of the drawbacks of the prior art compounds and methods.

A subject of the present invention is thus a liquid composition comprising, in an aqueous medium, one or more protein(s) and one or more solubilizing agent(s), wherein said solubilizing agent(s) is (are) chosen from the group consisting of anionic compounds of non-saccharide structure, said structure of which contains at least one aromatic nucleus comprising at least 6 ring members (6 atoms) and at least one carboxylic acid group in salified form, and which has, in its acid form, a molar mass of between 130 and 500 g/mol.

It also relates to the use of said solubilizing agent(s) for preparing compositions according to the invention.

It also relates to a process for solubilizing one or more protein(s), wherein at least one solubilizing agent chosen from the group consisting of anionic compounds of non-saccharide structure, said structure of which contains at least one aromatic nucleus comprising at least 6 ring members (6 atoms) and at least one carboxylic acid group in salified form, and which has, in its acid form, a molar mass of between 130 and 500 g/mol, is added to an aqueous protein preparation in order to solubilize the protein.

By virtue of their particular structure, said solubilizing agents interact with proteins and particularly notably increase their solubilization in water, thereby enabling the preparation of aqueous solutions containing proteins. These solutions may be clear, optionally including at the isoelectric point, or "pI", of the proteins under consideration.

The term "clear" is intended to mean devoid of any light-scattering object, said objects leading to a loss of recovery (measured by separative, for example electrophoretic or chromatographic, analytical techniques such as RP-HPLC) and/or leading to an increase in scattered intensities by DLS measurement.

The recovery by separative analytical techniques can be measured in the manner presented in the examples.

The scattered intensities can be measured in the manner presented in the examples.

The term "nonclear" is intended to mean the presence of light-scattering objects and/or the presence of macroscopic cloudiness evaluated by eye. This can be measured by the loss of recovery by separative analytical techniques, said objects being separable either by centrifugation or by filtration.

In the case of a nonclear liquid composition, the recovery by separative analytical techniques is less than 99% and/or the scattered light intensity at 173° and/or at 12.8° increases by more than 5%.

The proteins under consideration exhibit a decrease in their maximum solubility at the pI. This decrease in maximum solubility at the pI can be measured by means of the methods presented in the examples.

In particular, the process according to the invention makes it possible to substantially increase the concentrations at which the proteins can be solubilized in water at their isoelectric point.

In particular, the compositions obtained according to the invention are homogeneous with good solubilization of protein active agents, and are stable over time.

In addition, the solubilizing agents according to the invention are small compounds, which makes it possible to limit the increase in the viscosity of the aqueous composition. In particular, and this constitutes a particularly surprising aspect of the invention, the applicant has demonstrated that it is not necessary to use compounds of polymeric structure, in particular saccharide structure, in order to improve protein solubilization. Indeed, it was generally considered up until now that polymeric structures were preferable, whereas there was a risk with small compounds of there being too few sites of interaction with protein active ingredients.

The present invention has a particularly advantageous application in the pharmaceutical and veterinary fields since it provides solubilizing agents which allow the stabilization, administration and delivery of protein active ingredients in an aqueous solution, by methods that are simple to carry out.

The solubilizing agents according to the invention can exhibit a biodegradability that is sufficiently rapid and suitable for their use in the preparation of a wide category of pharmaceutical formulations, including for medicaments intended for chronic and/or high-frequency administration. These compounds can also comply with the constraints established by pharmaceutical regulations, in particular in terms of their stability under normal preservation and storage conditions, in particular in solution.

A subject of the present invention is also the preparation of the composition above, and the use thereof in the pharmaceutical or veterinary field.

Other subjects, characteristics, aspects and advantages of the invention will emerge even more clearly on reading the description and the examples which follow.

In what follows, and unless otherwise indicated, the limits of a range of values are included in said range, in particular in the expression "between".

Moreover, the expression "at least one" used in the present description is equivalent to the expression "one or more".

The solubilizing agents used in the invention are compounds of non-saccharide structure.

The term "non-saccharide structure" is intended to mean that these compounds do not contain in their structure any saccharide unit, whether in cyclic or open and reduced or oxidized form.

The term "saccharide unit" denotes pentoses, hexoses, uronic acids, and N-acetylhexosamines in cyclic or open and reduced or oxidized form.

The solubilizing agents used in the invention are anionic compounds. The term "anionic compound" denotes a chemical compound containing only negative charges, and no positive charge. In particular, in the case where the compound comprises one or more nitrogen atoms in its structure, said nitrogen atoms do not carry a positive charge.

The solubilizing agents used in the invention contain in their structure one or more aromatic nucleus or nuclei comprising at least 6 ring members, i.e. an aromatic ring or heterocycle comprising at least 6 atoms chosen from carbon, nitrogen, sulfur or oxygen. This or these aromatic nucleus or nuclei can be advantageously chosen from optionally substituted benzene nuclei and optionally substituted indole nuclei, and preferably optionally substituted benzene nuclei.

The aromatic nucleus or nuclei may be substituted or unsubstituted. The substituent(s) may be linear or branched, saturated or unsaturated, and cyclic or noncyclic. It/They may also be condensed or polycyclic, but must comprise at least one aromatic ring or heterocycle comprising at least 6 atoms chosen from carbon, nitrogen, sulfur or oxygen. These rings comprising at least 6 atoms chosen from carbon, nitrogen, sulfur or oxygen are defined in the present application as aromatic nuclei comprising at least 6 ring members.

The substituent(s) may in particular be chosen from —OH, and —OR$_1$ groups with R$_1$ denoting an alkyl or hydroxyalkyl radical containing from 1 to 6 carbon atoms.

Preferably, the aromatic nucleus is not substituted.

The solubilizing agents used in the invention also comprise in their structure one or more carboxylic acid group(s), in salt form, i.e. one or more groups of structure:

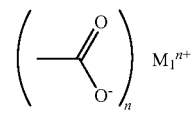

with $M_1^{n+}$ representing a cation, preferably a pharmaceutically acceptable cation, and n is an integer equal to 1 or 2.

According to one preferred embodiment, $M_1^{n+}$ denotes a cation chosen from $Ca^{2+}$, $Mg^{2+}$, $Na^+$ or $K^+$ and more preferentially $M_1^{n+}$ denotes $Na^+$ or $K^+$.

The solubilizing agents used in the invention have a molar mass of between 130 and 500 g/mol.

This molar mass corresponds to the acid form of the solubilizing agent, i.e. when the carboxylic acid group(s) is (are all) in acid form:

Preferably, the molar mass of the solubilizing agent(s) is between 130 and 450 g/mol, and preferentially between 130 and 400 g/mol.

According to one preferred embodiment, the solubilizing agents used in the invention are water-soluble. The term "water-soluble" is intended to mean that these agents have, in water at a pH of 7 and at 25° C., a minimum solubility of 50 mmol/l, preferably a minimum solubility of 100 mmol/l and more preferentially of 250 mmol/l.

According to one preferred embodiment, the solubilizing agent(s) used in the invention correspond(s) to general formula (I) below:

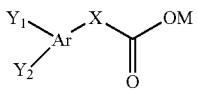
(I)

with:
Ar denotes an aromatic nucleus comprising at least 6 ring members;
X denotes a saturated or unsaturated, linear or branched divalent radical, the main chain of which consists of 1 to 4 carbon atoms and optionally 1 or 2 heteroatoms chosen from nitrogen and oxygen atoms, it being possible for said main chain to optionally bear one or more substituents;
$Y_1$ and $Y_2$ denote, independently of one another: a hydrogen atom; an —OH group; an —OR1 group with R1 denoting an alkyl radical containing from 1 to 6 carbon atoms or a hydroxyalkyl radical containing from 1 to 6 carbon atoms; and preferably $Y_1$ and $Y_2$ denote, independently of one another, a hydrogen atom or an —OH group; and
M denotes a cation such as, in particular, $Na^+$ or $K^+$.

Preferably, Ar denotes a benzene nucleus or an indole nucleus.

According to a first particularly preferred embodiment, Ar denotes a benzene nucleus. In this embodiment, the solubilizing agent(s) correspond(s) to formula (Ia) below:

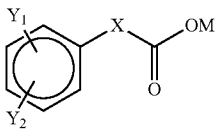
(Ia)

with X, $Y_1$, $Y_2$ and M as defined above.

According to a second preferred embodiment, Ar denotes an indole nucleus. In this embodiment, the solubilizing agent(s) preferably correspond(s) to formula (Ib) below:

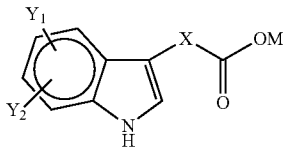
(Ib)

with X, $Y_1$, $Y_2$ and M as defined above.

In formulae (I), (Ia) and (Ib) above, the divalent radical X comprises a main chain, consisting of 1 to 4 carbon atoms and optionally 1 or 2 heteroatoms chosen from nitrogen and oxygen atoms. The carbon atoms constituting the main chain may be, independently of one another, saturated or unsaturated. The term "main chain" denotes a series of atoms comprising from 1 to 4 carbon atoms and linking, linearly, the aromatic group Ar to a carboxylate group —COOM.

As set out above, this main chain may bear one or more substituents, i.e. one or more atoms or groups of atoms other than a hydrogen atom.

The substituent(s) then advantageously correspond(s) to the general formula:

-L-Z with:
L denotes a single bond or a group chosen from an amide group —NHCO—, a carbamate group —NHCOO— or a urea group —NHCONH—; and
Z denotes a hydroxyl group (—OH); a saturated or unsaturated, linear or branched radical comprising from 1 to 4 carbon atoms, said carbon atoms bearing at least one hydroxyl group —[$CH_2$]$_X$—[OH]$_Y$; a salified carboxylic acid group (—COOM' with M'=$Na^+$ or $K^+$); or a saturated or unsaturated, linear or branched radical comprising from 1 to 12 carbon atoms and optionally one or more heteroatoms, such as, in particular, one or more oxygen atoms.

Preferably, L denotes a single bond or an amide group.

Preferably, Z is chosen from a hydroxyl group (—OH) or a saturated or unsaturated, linear or branched radical comprising from 1 to 4 carbon atoms which can optionally bear one or more hydroxyl groups (—OH) and/or salified carboxylic acid groups (—COOM" with M"=$Na^+$ or $K^+$).

According to one preferred embodiment, the solubilizing agent(s) correspond(s) to formula (Ia) above in which:
$Y_1$ and $Y_2$ both denote a hydrogen atom;
X denotes a saturated or unsaturated, linear divalent radical, the main chain of which consists of 1 to 4 carbon atoms and optionally one or two heteroatom(s) chosen from nitrogen and oxygen atoms, said chain not bearing any substituent other than hydrogen atoms.

In this embodiment, the main chain preferably consists of 1 or 2 carbon atoms and optionally a heteroatom chosen from nitrogen and oxygen atoms, and more preferentially the main chain consists of 1 or 2 carbon atoms.

According to another preferred embodiment, the solubilizing agent(s) correspond(s) to formula (Ia) above in which:
$Y_1$ and $Y_2$ both denote a hydrogen atom;
X denotes a saturated or unsaturated, branched divalent radical, the main chain of which consists of 1 to 4 carbon atoms and optionally one or two heteroatom(s) chosen from nitrogen and oxygen atoms, said chain bearing one or more substituents -L-Z as defined above.

In this embodiment, the main chain preferably consists of 1 or 2 carbon atoms and optionally a heteroatom chosen from nitrogen and oxygen atoms, and more preferentially the main chain consists of 1 or 2 carbon atoms.

In this embodiment, according to a first preferred variant, the main chain bears one or more, and preferably one, substituent(s) -L-Z, with L denoting an amide group and Z denoting a saturated or unsaturated, linear or branched radical comprising from 1 to 4 carbon atoms which can optionally bear one or more hydroxyl groups (—OH) and/or one salified carboxylic acid group (—COOM" with M"=$Na^+$ or $K^+$).

In this embodiment, according to a second variant which is likewise preferred, the main chain bears one or more substituent(s) -L-Z, L denoting a single bond and Z denoting a hydroxyl group (—OH); a salified carboxylic acid group (—COOM' with M'=Na$^+$ or K$^+$); or a saturated or unsaturated, linear or branched radical comprising from 1 to 12 carbon atoms and optionally bearing one or more hydroxyl groups (—OH) and/or one salified carboxylic acid group (—COOM" with M"=Na$^+$ or K$^+$).

In this second variant, Z preferably denotes a hydroxyl group (—OH) or a salified carboxylic acid group (—COOM' with M'=Na$^+$ or K$^+$).

The main chain of the divalent radical X may then, for example, bear:
- one or more hydroxyl group(s) (—OH); or
- one or more salified carboxylic acid groups (—COOM') and preferably one salified carboxylic acid group; or else
- one or more hydroxyl groups (—OH) and one or more salified carboxylic acid groups (—COOM') and preferably one hydroxyl group and one salified carboxylic acid group.

According to another preferred embodiment, the solubilizing agent(s) correspond(s) to formula (Ia) above in which:
- at least one of $Y_1$ and $Y_2$ denotes an —OH group, and preferably $Y_1$ denotes an —OH group and $Y_2$ denotes a hydrogen atom;
- X denotes a saturated or unsaturated, linear divalent radical, the main chain of which consists of 1 to 4 carbon atoms and optionally one or two heteroatom(s) chosen from nitrogen and oxygen atoms, said chain not bearing any substituent other than hydrogen atoms.

In this embodiment, the main chain preferably consists of 1 or 2 carbon atoms and optionally a heteroatom chosen from nitrogen and oxygen atoms, and more preferentially the main chain consists of 1 or 2 carbon atoms.

According to another preferred embodiment, the solubilizing agent(s) correspond(s) to formula (Ia) above in which:
- at least one of $Y_1$ and $Y_2$ denotes an —OH group, and preferably $Y_1$ denotes an —OH group and $Y_2$ denotes a hydrogen atom;
- X denotes a saturated or unsaturated, branched divalent radical, the main chain of which consists of 1 to 4 carbon atoms and optionally one or two heteroatom(s) chosen from nitrogen and oxygen atoms, said chain bearing one or more substituents -L-Z as defined above.

In this embodiment, the main chain preferably consists of 1 or 2 carbon atoms and optionally a heteroatom chosen from nitrogen and oxygen atoms, and more preferentially the main chain consists of 1 or 2 carbon atoms.

In this embodiment, according to a first preferred variant, the main chain bears one or more, and preferably one, substituent(s) -L-Z, with L denoting an amide group and Z denoting a saturated or unsaturated, linear or branched radical comprising from 1 to 4 carbon atoms which can optionally bear one or more hydroxyl groups (—OH) and/or one salified carboxylic acid group (—COOM" with M"=Na$^+$ or K$^+$).

In this embodiment, according to a second variant which is likewise preferred, the main chain bears one or more substituent(s) -L-Z, L denoting a single bond and Z denoting a hydroxyl group (—OH); a salified carboxylic acid group (—COOM' with M'=Na$^+$ or K$^+$); or a saturated or unsaturated, linear or branched radical comprising from 1 to 12 carbon atoms and optionally bearing one or more hydroxyl groups (—OH) and/or one salified carboxylic acid group (—COOM" with M"=Na$^+$ or K$^+$).

In this second variant, Z preferably denotes a hydroxyl group (—OH) or a salified carboxylic acid group (—COOM" with M'=Na$^+$ or K$^+$).

The main chain of the divalent radical X can then, for example, bear:
- one or more hydroxyl group(s) (—OH); or
- one or more salified carboxylic acid groups (—COOM') and preferably one salified carboxylic acid group; or else
- one or more hydroxyl groups (—OH) and one or more salified carboxylic acid groups (—COOM') and preferably one hydroxyl group and one salified carboxylic acid group.

According to one likewise preferred embodiment of the invention, the compound of formula (I) is resulting from a natural or synthetic amino acid bearing an aromatic ring.

Among the natural amino acids, the use of alpha-amino acids, such as phenylalanine, tyrosine and tryptophan, is quite particularly preferred.

According to one particularly preferred embodiment, the compound of formula (I) is resulting from phenylalanine.

According to one particularly preferred embodiment, the compound of formula (I) is resulting from tryptophan.

According to one embodiment, the compound of formula (I) is resulting from a synthetic amino acid and, in one embodiment, the synthetic amino acid is phenylglycine.

The amino acids can be used in the form of either of their optical isomers (L or D forms), or in the form of a mixture of such isomers, and in particular in racemate form.

Preferably, the solubilizing agent according to the invention is resulting from an amino acid of which the amine group has been converted into a group chosen from an amide group, a carbamate group or a urea group, or substituted.

Said amide, carbamate or urea group can be linked to a hydrogen atom or to a hydrocarbon-based substituent containing from 1 to 6 carbon atoms and optionally one or more oxygen atoms.

When the amine function is substituted, it can be substituted with a substituent chosen from the group consisting of $C_2$ to $C_4$ hydroxycarboxyls, in particular the hydroxyacetyl group.

Preferably, the solubilizing agent, and in particular the compound of formula (I), is resulting from an amino acid of which the amino group has been converted into an amide group. Preferably, said amide group is substituted with a hydrocarbon-based radical containing from 1 to 6, and preferably from 1 to 4, carbon atoms, and which can optionally bear one or more hydroxyl groups (—OH).

Two particularly preferred compounds are N-hydroxyacetylphenylalanine and N-hydroxyacetyltryptophan, corresponding to the formulae below:

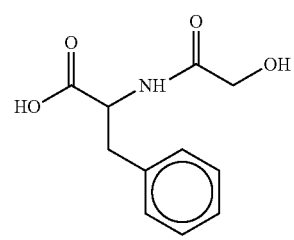

-continued

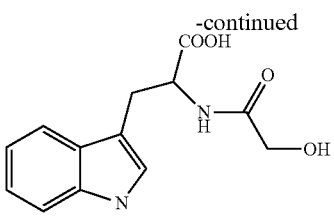

and used in sodium salt or potassium salt form.

According to one likewise preferred embodiment, the solubilizing agent, and in particular the compound of formula (I), is resulting from a phenol.

The composition according to the invention advantageously comprises the solubilizing agent(s) as described above in a total concentration of between 1 g/l and 100 g/l.

The invention also relates to a process for solubilizing one or more protein(s) in water, wherein at least one solubilizing agent chosen from the group consisting of anionic compounds of non-saccharide structure, said structure of which contains at least one aromatic nucleus comprising at least 6 ring members (6 atoms) and at least one carboxylic acid group in salified form, and which has, in its acid form, a molar mass of between 130 and 500 g/mol, is added to an aqueous protein composition in order to solubilize the protein.

The invention also relates to the use, in order to improve the solubilization of one or more protein(s) within an aqueous composition, of at least one solubilizing agent chosen from the group consisting of anionic compounds of non-saccharide structure, said structure of which contains at least one aromatic nucleus comprising at least 6 ring members (6 atoms) and at least one carboxylic acid group in salified form, and which has, in its acid form, a molar mass of between 130 and 500 g/mol.

The following embodiments apply both to the process for solubilizing one or more protein(s) within an aqueous composition and/or to their use.

In one embodiment, the process or the use according to the invention is one wherein at least one solubilizing agent corresponds to general formula (I) below:

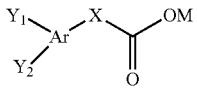
(I)

with:
Ar denoting an aromatic nucleus comprising at least 6 ring members;
X denoting a saturated or unsaturated, linear or branched divalent radical, the main chain of which consists of 1 to 4 carbon atom(s) and optionally 1 or 2 heteroatom(s) chosen from nitrogen and oxygen atoms, it being possible for said main chain to optionally bear one or more substituent(s);
$Y_1$ and $Y_2$ denoting, independently of one another: a hydrogen atom; an —OH group; an —OR1 group with R1 denoting an alkyl radical containing from 1 to 6 carbon atom(s) or a hydroxyalkyl radical containing from 1 to 6 carbon atom(s); and preferably $Y_1$ and $Y_2$ denote, independently of one another, a hydrogen atom or an —OH group; and
M denoting a cation such as, in particular, $Na^+$ or $K^+$.

In one embodiment, the process or the use according to the invention is one wherein, in formula (I), Ar denotes a benzene nucleus or an indole nucleus.

In one embodiment, the process or the use according to the invention is one wherein the solubilizing agent(s) correspond(s) to formula (Ia) below:

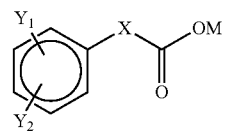
(Ia)

with:
X denoting a saturated or unsaturated, linear or branched divalent radical, the main chain of which consists of 1 to 4 carbon atom(s) and optionally 1 or 2 heteroatom(s) chosen from nitrogen and oxygen atoms, it being possible for said main chain to optionally bear one or more substituent(s);
$Y_1$ and $Y_2$ denoting, independently of one another: a hydrogen atom; an —OH group; an —OR1 group with R1 denoting an alkyl radical containing from 1 to 6 carbon atom(s) or a hydroxyalkyl radical containing from 1 to 6 carbon atom(s); and preferably $Y_1$ and $Y_2$ denote, independently of one another, a hydrogen atom or an —OH group; and
M denoting a cation such as, in particular, $Na^+$ or $K^+$.

In one embodiment, the process or the use according to the invention is one wherein the solubilizing agent(s) correspond(s) to formula (Ib) below:

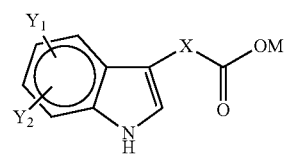
(Ib)

with:
X denoting a saturated or unsaturated, linear or branched divalent radical, the main chain of which consists of 1 to 4 carbon atom(s) and optionally 1 or 2 heteroatom(s) chosen from nitrogen and oxygen atoms, it being possible for said main chain to optionally bear one or more substituent(s);
$Y_1$ and $Y_2$ denoting, independently of one another: a hydrogen atom; an —OH group; an —$OR_1$ group with $R_1$ denoting an alkyl radical containing from 1 to 6 carbon atom(s) or a hydroxyalkyl radical containing from 1 to 6 carbon atom(s); and preferably $Y_1$ and $Y_2$ denote, independently of one another, a hydrogen atom or an —OH group; and
M denoting a cation such as, in particular, $Na^+$ or $K^+$.

In one embodiment, the process or the use according to the invention is one wherein, in formula (I), (Ia) or (Ib), the divalent radical X bears on its main chain one or more substituents corresponding to the general formula:

-L-Z with:
L denotes a single bond or a group chosen from an amide group —NHCO—, a carbamate group —NHCOO— or a urea group —NHCONH—; and
Z denotes a hydroxyl group (—OH); a saturated or unsaturated, linear or branched radical comprising from 1 to 4 carbon atoms, said carbon atoms bearing at least one hydroxyl group —[CH$_2$]$_X$—[OH]$_Y$; a salified carboxylic acid group (—COOM' with M'=Na$^+$ or K$^+$); or a saturated or unsaturated, linear or branched radical comprising from 1 to 12 carbon atoms and optionally one or more heteroatoms such as, in particular, one or more oxygen atoms.

In one embodiment, the process or the use according to the invention is one wherein L denotes a single bond or an amide group.

In one embodiment, the process or the use according to the invention is one wherein the solubilizing agent is resulting from a natural or synthetic amino acid bearing an aromatic ring, preferably chosen from phenylalanine, tyrosine and tryptophan, and more preferentially phenylalanine or tryptophan.

In one embodiment, the process or the use according to the invention is one wherein the solubilizing agent is chosen from the group consisting of N-hydroxyacetylphenylalanine and N-hydroxyacetyltryptophan, corresponding to the formulae below:

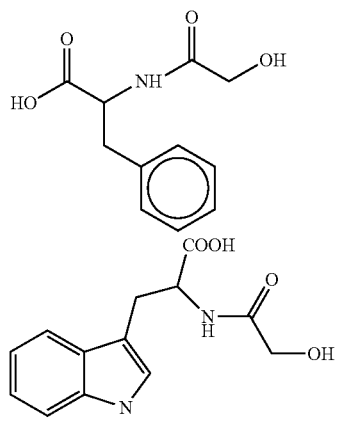

used in sodium salt or potassium salt form.

In one embodiment, the process or the use according to the invention is one wherein the solubilizing agent is resulting from a phenol.

In one embodiment, the process or the use according to the invention is one wherein the solubilizing agent is chosen from the following compounds, used in sodium salt or potassium salt form:

| Name | Structure |
|---|---|
| Phenylacetic acid | ![structure] |
| Mandelic acid | ![structure] |
| Hydrocinnamic acid | ![structure] |
| Trans-cinnamic acid | ![structure] |
| 2-Phenoxypropionic acid | ![structure] |
| 3-Phenyllactic acid | ![structure] |
| Phenylsuccinic acid | ![structure] |
| Alpha-hydroxyhippuric acid | ![structure] |

In one embodiment, the process or the use according to the invention is one wherein said aqueous composition comprises the solubilizing agent(s) in a total concentration of between 1 g/l and 100 g/l.

In one embodiment, the process or the use according to the invention is one wherein said aqueous composition contains a total concentration of protein(s) of between 0.5 and 400 mg/ml, preferably between 50 and 350 mg/ml.

In one embodiment, the process or the use according to the invention is one wherein the molar ratio between the total amount of solubilizing agent(s) and the total amount of protein(s) in the composition is greater than or equal to 20, preferably greater than or equal to 35, more preferentially greater than or equal to 45, even more preferentially greater than or equal to 100, more preferentially greater than or equal to 150, and even better still greater than or equal to 200.

In one embodiment, the process or the use according to the invention is one wherein said aqueous composition is intended to be administered by intravenous injection, by subcutaneous injection or by intramuscular injection, and preferably by subcutaneous injection.

The composition according to the invention also contains one or more protein(s).

The term "protein" denotes, in a manner known per se, a macromolecule composed of one or more chains of amino acids linked to one another by peptide bonds.

The proteins used in the invention may be of natural or synthetic origin.

The invention is quite particularly suitable for the solubilization of proteins containing at least 10, and preferably at least 50, amino acids.

Preferably, the proteins involved in the present invention have an isoelectric point of between 4 and 9, more preferentially between 4.5 and 8.5, and more particularly between 5.5 and 8.

The invention applies quite particularly to proteins which exhibit at their isoelectric point a decrease in their maximum solubility in water of at least 2%, preferably at least 5%, or even at least 10%. For such proteins, it is noted in particular by simple visual observation that an aqueous solution containing them goes from clear to cloudy when the pH of the solution approaches the isoelectric point of the protein.

According to one preferred embodiment of the invention, the protein(s) is (are) chosen from therapeutic proteins.

According to one preferred embodiment of the invention, the protein(s) is (are) chosen from proteins containing at least one antibody fragment.

The term "protein comprising at least one antibody fragment" is intended to mean a protein chosen from monoclonal antibodies (mAbs), polyclonal antibodies, fusion proteins, nanobodies, bispecific antibodies and antibodies coupled to cytotoxic active ingredients (ADCs—antibody-drug conjugates).

According to one embodiment of the present invention, the protein comprising at least one antibody fragment is a monoclonal antibody.

The term "monoclonal antibody" is intended to mean a complete antibody, an antibody fragment or an antibody derivative which has an identical and unique specificity, i.e. which recognizes just one type of epitope on a given antigen.

According to the present invention, a monoclonal antibody may also be called an immunoglobulin (hereinafter Ig).

The term "complete antibody" is intended to mean an antibody composed of two identical heavy chains and of two identical light chains which are linked by a disulfide bridge. Each chain consists, in the N-terminal position, of a variable region (or domain) (encoded by the rearranged V-J genes for the light chains and the rearranged V-D-J genes for the heavy chains) specific for the antigen against which the antibody is directed, and, in the C-terminal position, of a constant region, consisting of a single CL domain for the light chains or of several domains for the heavy chains. Each variable region comprises three segments called "complementarity determining regions" ("CDRs") or "hypervariable regions", which are mainly responsible for the binding to the epitope of an antigen. The two heavy (H) chains and the two light (L) chains are identical to one another. The light chain is composed of 2 domains, a variable domain V and a constant domain C, folded in space independently of one another. They are called VL and CL. The heavy chain also comprises a domain V denoted VH and 3 or 4 domains C denoted from CH1 to CH4. Each domain comprises approximately 110 amino acids and is structured comparably. The 2 heavy chains are linked by disulfide bridges and each heavy chain is linked to a light chain, also by a disulfide bridge. The region which determines the specificity of the antibody for the antigen is carried by the variable parts, while the constant parts can interact with the Fc receptors of effector cells or of molecules such as complement in order to mediate various functional properties. The term "VH" refers to the variable regions of an immunoglobulin heavy chain of an antibody, including the heavy chains of an Fv, scFv, dsFv, Fab, Fab' or F(ab)' fragment. The term "VL" refers to the variable regions of an immunoglobulin light chain of an antibody, including the light chains of an Fv, scFv, dsFv, Fab, Fab' or F(ab)' fragment. The term "CDR regions" or "CDRs" is intended to denote the hypervariable regions of the heavy and light chains of immunoglobulins as defined by Kabat et al. (Kabat et al., Sequences of proteins of immunological interest, 5th ed., U.S. Department of Health and Human Services, NIH, 1991, and later editions). There are 3 heavy-chain CDRs and 3 light-chain CDRs. The term CDR or CDRs is used herein to denote, as appropriate, one of these regions or several, or even all, of these regions which contain the majority of the amino acid residues responsible for the affinity binding of the antibody for the antigen or the epitope that it recognizes. The most conserved regions of the variable domains are called FR (for "framework") regions or sequences and there are 4 of them (FR1 to FR4).

Antibodies are subdivided into 5 classes or isotypes: IgG, IgA, IgM, IgE and IgD according to the structure of the heavy-chain constant domains, i.e. respectively γ, α, µ, ε and δ chains.

The IgG and IgA classes are, moreover, subdivided into subclasses according in particular to the size of the hinge regions and also the number and position of disulfide bridges between heavy chains.

The IgG class is subdivided into 4 subclasses, i.e. IgG1, IgG2, IgG3 and IgG4.

The IgA class is, for its part, subdivided into 2 subclasses, i.e. IgA1 and IgA2.

Preferably, the protein comprising at least one antibody fragment is a monoclonal antibody chosen from IgGs, IgAs, IgMs, IgEs and IgDs. The IgAs can be chosen from IgA1s and IgA2s, and the IgGs can be chosen from IgG1s, IgG2s, IgG3s and IgG4s.

In one embodiment, the monoclonal antibody is an IgG.
In one embodiment, the monoclonal antibody is an IgA.
In one embodiment, the monoclonal antibody is an IgM.
In one embodiment, the monoclonal antibody is an IgE.
In one embodiment, the monoclonal antibody is an IgD.
In one embodiment, the monoclonal antibody is an IgG1.
In one embodiment, the monoclonal antibody is an IgG2.
In one embodiment, the monoclonal antibody is an IgG3.
In one embodiment, the monoclonal antibody is an IgG4.
In one embodiment, the monoclonal antibody is an IgA1.
In one embodiment, the monoclonal antibody is an IgA2.

The term "antibody fragment" is intended to mean any functional antibody fragment, e.g. Fab (Fragment, antigen binding), Fv, scFv (single chain Fv), Fc (Fragment, crystallizable), F(ab')2, Fab', scFv-Fc, synthetic polypeptides containing the sequences of one or more CDRs, which generally have the same binding specificity as the antibody from which they are derived.

The antibody fragments used in the invention can be obtained from the antibodies by methods such as digestion with enzymes, for instance pepsin or papain, and/or by disulfide-bridge cleavage by chemical reduction. The enzymatic digestion of antibodies with papain generates 2 identical fragments, which are called "Fab fragment" (Fragment, antigen binding), and an Fc fragment (Fragment, crystallizable). The Fc fragment is the support for the effector functions of immunoglobulins. Digestion with pepsin generates an F(ab')2 fragment, where the two Fab fragments remain linked by two disulfide bridges, and the Fc fragment is split up into several peptides. The F(ab')2 fragment is made up of two Fab' fragments, linked by inter-chain disulfide bridges so as to form one F(ab')2.

Thus, the monoclonal antibody or antibodies according to the invention can advantageously contain one or more of these fragments, and all the combinations between the abovementioned fragments can be used in the context of the present invention.

The term "antibody derivative" is intended to mean any antibody, it being possible for this antibody to comprise one or more mutations, substitutions, deletions and/or additions of one or more amino acid residues. Such an addition, substitution or deletion can be located at any position in the molecule. In the case where several amino acids have been added, substituted or deleted, any combination of addition, substitution or deletion can be considered, provided that the resulting antibody still has at least the advantageous properties of the antibody of the invention.

According to the invention, the monoclonal antibody can advantageously be a chimeric antibody or a humanized antibody. The term "chimeric antibody" is intended to mean an antibody of which the heavy- and light-chain variable regions, or at least one domain or fragment of these regions, belong to a species different than the species to which the constant regions of the light chains and of the heavy chains belong. The term "humanized antibody" is intended to mean an antibody which contains mainly human immunoglobulin sequences. This term generally refers to a non-human immunoglobulin which has been modified by incorporation of human sequences or of residues found in human sequences.

The antibodies described above can, for example, be obtained using the standard recombinant DNA techniques well known to those skilled in the art, for example using the techniques for constructing chimeric antibodies described, for example, in Morrison et al., Proc. Natl. Acad. Sci. U.S.A., 81, pp. 6851-55 (1984), where recombinant DNA technology is used to replace the constant region of a heavy chain and/or the constant region of a light chain of an antibody originating from a non-human mammal, with the corresponding regions of a human immunoglobulin. Such antibodies and the method for preparing them have also been described in patent application EP 173 494, in the document Neuberger, M. S. et al., Nature 312 (5995): 604-8 (1985), and also in document EP 125 023, for example. Methods for generating chimeric antibodies are widely available to those skilled in the art. For example, the heavy and light chains of the antibody can be expressed separately using a vector for each chain, or else can be integrated into a single vector.

By way of example, among the commercially available monoclonal antibodies, mention will be made of the following monoclonal antibodies: Muromonab-CD3 (sold under the name Orthoclone Okt3®), Abciximab (sold under the name Reopro®), Rituximab (sold under the names Mab-Thera® and Rituxan®), Basiliximab (sold under the name Simulect®), Daclizumab (sold under the name Zenapax®), Palivizumab (sold under the name Synagis®), Infliximab (sold under the name Remicade®), Trastuzumab (sold under the name Herceptin®), Alemtuzumab (sold under the names MabCampath®, Campath-1H®), Adalimumab (sold under the name Humira®), Tositumomab-I131 (sold under the name Bexxar®), Efalizumab (sold under the name Raptiva®), Cetuximab (sold under the name Erbitux®), Ibritumomab tiuxetan (sold under the name Zevalin®), Omalizumab (sold under the name Xolair®), Bevacizumab (sold under the name Avastin®), Natalizumab (sold under the name Tysabri®), Ranibizumab (sold under the name Lucentis®), Panitumumab (sold under the name Vectibix®), Eculizumab (sold under the name Soliris®), Certolizumab pegol (sold under the name Cimzia®), Golimumab (sold under the name Simponi®), Canakinumab (sold under the name Ilaris®), Catumaxomab (sold under the name Removab®), Ustekinumab (sold under the name Stelara®), Tocilizumab (sold under the names RoActemra®, and Actemra®), Ofatumumab (sold under the name Arzerra®), Denosumab (sold under the name Prolia®), Belimumab (sold under the name Benlysta®), Raxibacumab (not yet marketed), Ipilimumab (sold under the name Yervoy®) and Pertuzumab (sold under the name Perjeta®).

According to one embodiment of the present invention, the protein comprising at least one antibody fragment is a polyclonal antibody.

The term "polyclonal antibody" is intended to mean a mixture of whole antibodies, a mixture of antibody fragments or a mixture of antibody derivatives, as described above, recognizing various types of epitopes on a given antigen.

According to one embodiment of the present invention, the protein comprising at least one antibody fragment is a fusion protein.

The term "fusion protein" is intended to mean a construction which contains several proteins or polypeptides of different origin. This fusion protein is encoded by a nucleic acid obtained by recombinant DNA techniques well known to those skilled in the art. According to the present invention, the fusion protein is made up of a monoclonal antibody fragment as previously described and a fragment of a protein of interest.

By way of example, mention will be made of the fusion protein made up of a monoclonal antibody fragment which is the Fc region of an IgG1 immunoglobulin and a fragment of a protein of interest which is the extracellular domain of the CTLA-4 (Cytotoxic T-Lymphocyte Antigen 4) protein receptor, this fusion protein, i.e. abatacept, being sold under the name Orencia®.

By way of example, mention may also be made of the fusion protein made up of a monoclonal antibody fragment which is the Fc region of an IgG1 and a fragment of a protein of interest which is the P75 fraction of the soluble TNF-alpha receptor, this fusion protein, i.e. etanercept, being sold under the name Enbrel®.

By way of example, mention will also be made of the fusion protein made up of a monoclonal antibody fragment which is the Fc region of an IgG1 and a fragment of a protein of interest which is the extracellular portions of IL-1R1 (interleukin-1 receptor component) and of IL-1RAcP (IL-1 receptor accessory protein), this fusion protein, i.e. rilonacept, being sold under the name Arcalyst®.

By way of example, mention will also be made of the fusion protein made up of a monoclonal antibody fragment which is the IgG1 hinge, C(H)2 and C(H)3 regions, and a fragment of a protein of interest which is the extracellular domain of LFA-3, this fusion protein, i.e. alefacept, being sold under the name Amevive®.

According to one embodiment of the present invention, the protein comprising at least one antibody fragment is a nanobody.

The term "nanobody" is intended to mean any unique variable domain of immunoglobulin heavy chains. Nanobodies are more widely described in the publication D. Saerens and S. Muyldermans (eds.) *Single Domain Antibodies: Methods and Protocols*, Methods in Molecular Biology, vol. 911; and Med Microbiol Immunol (2009).

According to one embodiment of the present invention, the protein comprising at least one antibody fragment is a bispecific antibody.

The term "bispecific antibody" (also called bifunctional antibody or "diabody") is intended to mean any immunoglobulin fragment comprising 2 antigen-presenting sites. Bifunctional antibodies are more widely described in the publication Hollinger et al., Proc. Natl. Acad. Sci. USA 90: 6444-6448 (1993).

According to one embodiment of the present invention, the protein comprising at least one antibody fragment is an antibody coupled to a cytotoxic active ingredient.

The expression "antibody coupled to a cytotoxic active ingredient" is intended to mean a monoclonal antibody as previously described, coupled to a cytotoxic active ingredient.

By way of example of a cytotoxic active ingredient, mention may in particular be made of vedotin.

An example of an antibody coupled to a cytotoxic active ingredient is the antibody brentuximab coupled to the cytotoxic active ingredient vedotin. This antibody coupled to this cytotoxic active ingredient is sold under the name Adcetris®.

According to one likewise preferred embodiment of the invention, the protein(s) is (are) chosen from hormones.

Mention may in particular be made of: insulin; growth factors such as BMPs (Bone Morphogenetic Proteins), PDGFs (Platelet-Derived Growth Factors), coagulation factors and parathyroid hormones.

The protein(s) is (are) present in the composition according to the invention in solubilized form.

Generally, the composition according to the invention contains a total concentration of protein(s) of between 0.5 and 400 mg/ml.

Preferably, the total concentration of protein(s) is between 50 and 350 mg/ml, in particular between 80 and 250 mg/ml, preferably between 80 and 200 mg/ml, more preferentially between 100 and 200 mg/ml, better still between 120 and 200 mg/ml, and even better still between 120 and 180 mg/ml.

According to one particularly advantageous embodiment of the invention, the concentration of the protein in the composition is greater than the maximum concentration of the same protein in an aqueous solution at its isoelectric point, at a temperature of 25° C.

Typically, the protein is present in the composition at an osmolality of less than or equal to 700 mosmol/l, in particular less than or equal to 500 mosmol/l, or even less than or equal to 350 mosmol/l.

Typically, the protein is present in the composition at an osmolality of greater than or equal to 150 mosmol/l, in particular greater than or equal to 200 mosmol/l, or even greater than or equal to 250 mosmol/l.

Typically, the protein is present in the composition at an osmolality of between 150 and 700 mosmol/l, in particular of between 200 and 500 mosmol/l, or even of between 250 and 350 mosmol/l.

The osmolality can be measured using a Foske Micro-Osmometer instrument—Model 210.

In addition, the molar ratio between the total amount of solubilizing agent(s) and the total amount of protein(s) in the composition is advantageously greater than or equal to 20, preferably greater than or equal to 35, and more preferentially greater than or equal to 45.

More particularly, the molar ratio between the total amount of solubilizing agent(s) and the total amount of protein(s) in the composition is greater than or equal to 100, preferably greater than or equal to 150, and more preferentially greater than or equal to 200.

The composition according to the invention comprises an aqueous medium, i.e. it comprises water as main constituent. Advantageously, the composition comprises more than 50% by weight of water, preferably at least 70% by weight of water, more preferentially at least 80% by weight of water and even better still at least 90% by weight of water, relative to its total weight.

The water used in the composition may in particular be sterile water for injection or bacteriostatic water for injection.

Generally, the pH of the composition according to the invention may range from 4 to 8.

According to one embodiment of the invention, the pH of the composition is between 5 and 6.5.

According to another embodiment, the pH is between 5 and 8, preferably between 6 and 7.5, and more preferentially between 6 and 7.

The pH of the composition can be adjusted in a manner known per se by the addition of acids, of bases and/or of buffer systems, which are preferably pharmaceutically acceptable.

The composition according to the invention advantageously has a viscosity, measured at 25° C. and at atmospheric pressure, of less than or equal to 20 cP.

According to one embodiment, the composition according to the invention comprises one or more pharmaceutically acceptable acid(s).

These acids can in particular be chosen from hydrochloric acid, phosphoric acid, citric acid, acetic acid, ascorbic acid, ethylenediaminetetraacetic acid (also called EDTA) and tartaric acid.

According to one embodiment, the composition according to the invention comprises one or more pharmaceutically acceptable base(s).

These bases can in particular be chosen from inorganic bases formed from metals such as sodium, potassium, calcium or magnesium, and in particular from the group consisting of sodium hydroxide (NaOH), potassium hydroxide (KOH), and magnesium hydroxide ($Mg(OH)_2$).

Additionally, the pharmaceutically acceptable acids and/or bases include those resulting from amino acids, for instance histidine, arginine or glycine.

According to one embodiment, the composition according to the invention comprises a pharmaceutically acceptable buffer system. These pharmaceutically acceptable buffer systems include those which are resulting from the salts of the abovementioned acids and bases or from the combination thereof.

The buffer system can in particular be chosen from the following combinations: monobasic sodium phosphate (also called monosodium phosphate)/dibasic sodium phosphate (also called disodium phosphate), monobasic potassium phosphate (also called monopotassium phosphate)/dibasic sodium phosphate (also called disodium phosphate)/sodium salt, acetic acid/sodium acetate, citric acid/sodium citrate, L-histidine hydrochloride/histidine, glycine hydrochloride/glycine.

The composition according to the invention may also comprise one or more inorganic salt(s), preferably chosen from pharmaceutically acceptable inorganic salt(s).

Such salts may in particular be chosen from sodium chloride, potassium chloride and tin(II) chloride.

The composition according to the invention may comprise the protein(s) as sole therapeutic active agent. It may also comprise other therapeutic active agents in addition to the protein(s).

The composition according to the invention may also comprise any additive, adjuvant or excipient, which is preferably pharmaceutically acceptable.

Those skilled in the art will take care to select this or these optional additional compound(s) and/or active agent(s) in such a way that the advantageous properties intrinsically associated with the composition according to the invention are not, or not substantially, impaired by the envisioned addition(s).

Such additives may generally be present in an amount, for each of them, of between 0 and 10% by weight relative to the total weight of the composition.

In particular, the composition according to the invention may also comprise at least one preservative.

The preservative(s) may in particular be chosen from benzyl alcohol, phenol, m-cresol and povidone.

The composition according to the invention may also comprise at least one surfactant.

The surfactant(s) may be, for example, chosen from polysorbate 20 (also called PS20 or Tween 20), polysorbate 80 (also called PS80 or Tween 80), Pluronic F-68, the "Brij" products and also alkylglucosides such as n-dodecyl-a-D-maltoglucoside (DDM).

The composition according to the invention may also comprise a lyoprotectant and/or a pharmaceutically acceptable sugar.

The lyoprotectant and the pharmaceutically acceptable sugar may for example be chosen from α-trehalose, saccharose (also called sucrose), maltose, mannitol, sorbitol and dextran. Use may also be made, as lyoprotectant, of amino acids such as histidine.

According to one particularly preferred embodiment, the composition according to the invention is intended for therapeutic use, in humans or animals.

The composition according to the invention is then a pharmaceutical or veterinary composition, preferably a pharmaceutical composition.

In this embodiment, the composition according to the invention is preferably intended for systemic administration. It is in particular an injectable composition, intended to be administered, for example, by intravenous injection, by subcutaneous injection or by intramuscular injection, and more preferentially by subcutaneous injection.

Particularly preferably, the composition according to the invention is intended for therapeutic use in human beings.

A subject of the present invention is also the composition as described above, for use as a medicament.

According to one preferred embodiment, a subject of the invention is the composition as described above, for use in preventing and/or treating one or more pathological conditions in humans or animals.

The composition is particularly of use for treating all human pathological conditions involving the administration, to the patient, of one or more therapeutic proteins. In particular, and in a nonlimiting manner, the composition according to the invention may be used for treating the various forms of cancer, diabetes, autoimmune diseases, Alzheimer's disease, Crohn's disease, cardiovascular diseases, anemias, graft rejections, scleroses and rheumatoid arthritis.

The composition according to the invention can be prepared by simple mixing of its ingredients in water, with stirring.

It can in particular be prepared by mixing the solubilizing agent(s) and the protein(s) in water, at a pH which is preferably different than the isoelectric point of the protein(s) under consideration. The pH can then be adjusted if required.

Finally, the invention relates to the use, in order to improve the solubilization of proteins within an aqueous composition, of a solubilizing agent consisting of an anionic compound of non-saccharide structure, which contains at least one aromatic nucleus comprising at least 6 ring members and at least one carboxylic acid group in salified form, and which has, in its acid form, a molar mass of between 130 and 500 g/mol.

Everything which has been described above regarding the composition according to the invention applies by analogy to the use according to the invention.

The following examples serve to illustrate the invention without, however, being limiting in nature.

EXAMPLES

Part A: Synthesis

Example A1

Molecule A1

The molecule A1 or N-(2-hydroxyacetyl)-L-phenylalanine is obtained from the methyl ester of L-phenylalanine, hydrochloride salt (Bachem) and from glycolic acid (Alfa Aesar) according to the process described in the article Pratt R. F. et al. *Biochemistry*, 2006, 45, 13074-13082.

Yield: 7.5 g (77%)

$^1$H NMR (DMSO-$d_6$, ppm): 3.00-3.20 (2H); 3.80 (1H); 4.55 (1H); 5.60 (1H); 7.15-7.50 (5H); 7.70 (1H); 12.90 (1H).

Example A2

Molecule A2

The molecule A2 or N-(2-hydroxyacetyl)-L-tryptophan is obtained from the methyl ester of L-phenylalanine, hydrochloride salt (Bachem) and from glycolic acid (Alfa Aesar) according to the process described in the article Pratt R. F. et al. *Biochemistry*, 2006, 45, 13074-13082.

Yield: 2.1 g (42%)

$^1$H NMR (DMSO-$d_6$, ppm): 3.25 (2H); 3.80 (2H); 4.60 (1H); 5.55 (1H); 6.99-7.55 (5H); 7.65 (1H); 10.90 (1H); 12.75 (1H).

Part B: Preparation of the Solutions of Compounds used in the Following Examples

|  | CAS number | Supplier | Reference | Stock solution concentration |
|---|---|---|---|---|
| Molecule A1 | 20917-41-3 | Adocia | — | 315 mg/ml |
| Sucrose | 57-50-1 | Sigma | S3929 | 800 mM |
| L-histidine | 71-00-1 | Sigma | H6034 | 200 mM |
| Mandelic acid | 90-64-2 | Aldrich | M2101 | 1000 mM |
| Acetic acid | 64-19-7 | Roth | 3738.1 | 1000 mM |
| Phenylacetic acid | 103-82-2 | Aldrich | P16621 | 900 mM |
| 2-Phenoxy-propionic acid | 940-31-8 | Aldrich | 197149 | 1125 mM |
| Molecule A2 | 70134-21-3 | Adocia | — | 315 mg/ml |

Example B1

Preparation of a Solution of the Molecule A1 at 315 mg/ml

The solid form of the molecule A1 is solubilized in sodium hydroxide at 1 mol/l, and then by adding sodium hydroxide at 10 mol/l, so as to obtain a solution at 315 mg/ml at pH 5.1.

Example B2

Preparation of a Solution of Sucrose at 800 mM

The sucrose (CAS 57-50-1, Sigma ref S3929) is solubilized in water at a concentration of 800 mM.

Example B3

Preparation of a Solution of L-Histidine at 200 mM

The L-histidine (CAS 71-00-1, Sigma ref H6034) is solubilized in water at a concentration of 200 mM. The solution obtained has a pH of 6.5.

Example B4

Preparation of the Solution of Mandelic Acid at 1000 mM

The mandelic acid (CAS 90-64-2, Aldrich ref M2101) is solubilized in sodium hydroxide at 1 mol/l, and then by adding sodium hydroxide at 10 mol/l, so as to obtain a solution at 1000 mM at pH 5.1.

Example B5

Preparation of the Solution of Acetic Acid at 1000 mM

The acetic acid (CAS 64-19-7, Roth ref 3738.1) is diluted in water to 1000 mM.

Example B6

Preparation of the Solution of Phenylacetic Acid at 900 mM

The phenylacetic acid (CAS 103-82-2, Aldrich ref P16621) is solubilized in sodium hydroxide at 1 mol/l so as to obtain a solution at 900 mM at pH 5.9.

Example B7

Preparation of the Solution of 2-phenoxypropionic Acid at 1125 mM

The 2-phenoxypropionic acid (CAS 940-31-8, Aldrich ref 197149) is solubilized in sodium hydroxide at 1 mol/l, and then by adding sodium hydroxide at 10 mol/l, so as to obtain a solution at 1000 mM at pH 12.5.

Example B8

Preparation of a Solution of the Molecule A2 at 315 mg/ml

The solid form of the molecule A2 is solubilized in sodium hydroxide at 1 mol/l, and then by adding sodium hydroxide at 10 mol/l, so as to obtain a solution at 315 mg/ml at pH 5.1.

Part C: Solubilization of Proteins at their Isoelectric Points

Example C1

Solubilization of Human Insulin at its Isoelectric Point

Human insulin has an isoelectric point (pI) of 5.3. At the pH of 5.3, human insulin precipitates at a concentration of greater than or equal to 10 IU/ml. A test of solubility at the pI of human insulin with various compounds is carried out.

A solution of human insulin at 500 IU/ml is prepared. Solutions of compounds at various concentrations in water are prepared as described in examples B1 to B4. Mixing between a solution of human insulin and the solution of compound is carried out in order to obtain a solution containing 100 IU/ml of human insulin and the desired concentration of compound. The pH of the various solutions is adjusted to pH 5.3 by adding hydrochloric acid or sodium hydroxide depending on the pH achieved following the mixing between the compound and the solution of human insulin.

The appearance of the solution is documented. If the solution is cloudy, the compound at the concentration tested does not allow total solubilization of human insulin at its isoelectric point. If the solution is clear, the compound allows total solubilization of human insulin at the concentration tested. In addition, the mixtures are centrifuged at 4000 rpm for 10 minutes in a Hereaus Biofuge Pico centrifuge (Rotor #3328) and then filtered through 0.22 μm in order to remove the precipitate. The resulting soluble fractions are then assayed by RP-HPLC (column: Sunfire C18, Waters ref:186003417; mobile phase: sodium phosphate/acetonitrile gradient; detection: UV at 276 nm) with an external insulin range in order to quantify the percentage of soluble insulin at the pI. The results obtained (appearance and soluble percentages) are given in table 1.

TABLE 1

| Mixtures | Molar ratio (compound/insulin) | Compound concentration (mmol/l) | Visual appearance | Soluble insulin recovery (%) |
|---|---|---|---|---|
| Human insulin control | — | — | Cloudy | 11 |
| Molecule A1 | 500 | 300 | Clear | 100 |
| Mandelic acid | 1250 | 750 | Clear | 100 |
| Sucrose | 250 | 150 | Cloudy | 67 |
| Sucrose | 500 | 300 | Cloudy | 35 |
| Histidine | 125 | 75 | Cloudy | 48 |
| Molecule A2 | 200 | 120 | Clear | 100 |

The examples with the molecule A1, with the molecule A2 and with mandelic acid (according to the invention) demonstrate a very strong improvement in the solubility of human insulin at its pI. Indeed, they result in clear solutions of insulin at its isoelectric point with an insulin concentration above its maximum solubility at the pI.

Example C2

Reduction in the Aggregation of a Formulation of Human Immunoglobulins (Nanogam) at its Isoelectric Point The Nanogam formulation is a formulation of human immunoglobulins at 50 mg/ml and at pH 4.3 containing various IgG subclasses (IgG1: 54-70%, IgG2: 29-45%, IgG3: 1-4%, IgG4: 0-0.5%, IgA: at most 6 µg/ml). The isoelectric point of this composition is approximately 8.5. At this pH of 8.5, the immunoglobulins have a tendency to aggregate. A test with various compounds is therefore carried out at the isoelectric point in order to identify the compounds which make it possible to reduce this aggregation phenomenon.

A commercial solution of Nanogam at 50 mg/ml is used. Solutions of compounds at various concentrations are prepared as described in the examples B1-2 and B3-B7. Mixing between the solution of Nanogam and one of the solutions of compound is carried out in order to obtain a solution containing 40 mg/ml of human immunoglobulins and the desired concentration of compound. The pH of the various solutions is adjusted to pH 8.5 by adding hydrochloric acid or sodium hydroxide depending on the pH achieved following the mixing between the compound of interest and the solution of human immunoglobulins.

The mixtures are then analyzed by light scattering on a Malvern NanoZS instrument. The results obtained (scattered intensities at 12.8° standardized, i.e. Iscat 12.8° Mixture/Iscat 12.8° Nanogam at pH 4.3) are given in table 2.

The scattered intensities are measured at 12.8°. This angle of measurement is selected since it is sensitive to the largest nanoparticles/microparticles in suspension, such as the fibrils which appear at the isoelectric point of the Nanogam.

TABLE 2

| Mixtures | Molar ratio (COMPOUND/ NANOGAM) | Compound concentration (mmol/l) | Iscat 12.8° standardized |
| --- | --- | --- | --- |
| Nanogam control | — | — | 65.31 |
| Compound A1 | 320 | 85 | 23.5 |
| Mandelic acid | 675 | 27.5 | 22.15 |
| Phenylacetic acid | 675 | 180 | 20.082 |
| 2-Phenoxy-propionic acid | 675 | 180 | 6.38 |
| Histidine | 150 | 40 | 80.82 |
| Acetic acid | 675 | 180 | 200.18 |

The examples with the molecule A1, mandelic acid, phenylacetic acid and 2-phenoxypropionic acid show a very strong improvement of the solubility of Nanogam at its isoelectric point, whereas the examples with histidine and acetic acid do not demonstrate any improvement of the solubilization of Nanogam at its isoelectric point.

What is claimed is:

1. A process for solubilizing one or more protein(s) in water, comprising adding to an aqueous protein composition, at least one solubilizing agent selected from the group consisting of a sodium salt or a potassium salt of the formulae below:

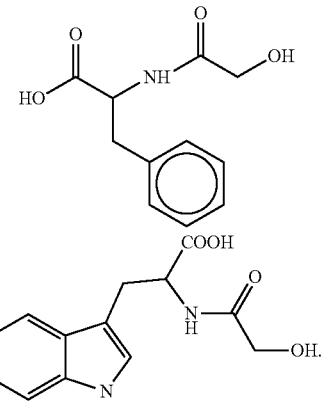

2. The process as claimed in claim 1, wherein said aqueous composition comprises the solubilizing agent(s) in a total concentration of between 1 g/l and 100 g/l.

3. The process as claimed in claim 1, wherein said aqueous composition contains a total concentration of protein(s) of between 0.5 and 400 mg/ml.

4. The process as claimed in claim 1, wherein the molar ratio between the total amount of solubilizing agent(s) and the total amount of protein(s) in the composition is greater than or equal to 20.

5. The process as claimed in claim 1, wherein said aqueous composition is adapted in a form to be administered by intravenous injection, by subcutaneous injection or by intramuscular injection.

6. A liquid composition comprising, in an aqueous medium, one or more protein(s) chosen from proteins containing at least one antibody fragment from monoclonal antibodies (mAbs), polyclonal antibodies, fusion proteins, nanobodies, bispecific antibodies and antibodies coupled to cytotoxic active ingredients (ADCs—antibody-drug conjugates) and one or more solubilizing agent(s)

selected from the group consisting of a sodium salt or a potassium salt of the formulae below:

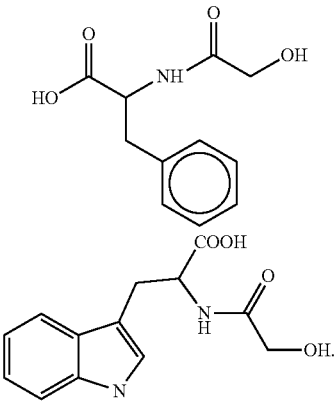

7. The composition as claimed in claim 6, which comprises the solubilizing agent(s) in a total concentration of between 1 g/l and 100 g/l.

8. The composition as claimed in claim 6, which contains a total concentration of protein(s) of between 0.5 and 400 mg/ml.

9. The composition as claimed in claim 6, wherein the molar ratio between the total amount of solubilizing agent(s) and the total amount of protein(s) in the composition is greater than or equal to 20.

10. The composition as claimed in claim 6, which is adapted in a form to be administered by intravenous injection, by subcutaneous injection or by intramuscular injection.

* * * * *